United States Patent [19]

Koshida et al.

[11] 4,382,967

[45] May 10, 1983

[54] METHOD FOR PREPARING POROUS SACCHARIDE GRANULES AND FOODS THEREFROM

[75] Inventors: Daikichi Koshida, Toyonaka; Ko Sugisawa, Nara; Yasushi Matsumura, Nara; Takashi Kimura, Nara; Kazumitsu Taga, Neyagawa, all of Japan

[73] Assignee: House Food Industrial Company Limited, Osaka, Japan

[21] Appl. No.: 229,017

[22] Filed: Jan. 27, 1978

[30] Foreign Application Priority Data

Jan. 28, 1980 [JP] Japan .................................. 55-7728
Jun. 25, 1980 [JP] Japan ................................ 55-85187
Sep. 4, 1980 [JP] Japan .............................. 55-121781
Sep. 4, 1980 [JP] Japan .............................. 55-121782

[51] Int. Cl.³ .......................... A23G 3/00; A23L 1/40
[52] U.S. Cl. ..................................... 426/96; 426/98; 426/103; 426/555; 426/589; 426/658; 426/445; 426/456; 426/465; 127/63; 127/30

[58] Field of Search ................... 426/589, 96, 658, 98, 426/103, 445, 456, 465, 639, 555; 127/63, 30

[56] References Cited

U.S. PATENT DOCUMENTS

| | | | |
|---|---|---|---|
| 215,944 | 5/1879 | Liebert | 426/589 |
| 2,901,382 | 8/1959 | Rohwer et al. | 127/63 |
| 2,901,389 | 10/1959 | Lachmann | 127/63 |
| 3,085,914 | 4/1963 | Wadsworth | 427/63 |
| 3,116,151 | 12/1963 | Giddey et al. | 426/589 |
| 3,212,908 | 10/1965 | Childs | 127/63 |
| 3,582,362 | 6/1971 | Drews | 426/589 |
| 4,213,249 | 7/1980 | Carse | 127/63 |

*Primary Examiner*—Jeanette M. Hunter
*Attorney, Agent, or Firm*—Oblon, Fisher, Spivak, McClelland & Maier

[57] ABSTRACT

Porous saccharide granules prepared by moistening saccharide granules and heating to crystallize the granules said porous granules having oil adsorbed therein and cake mixes and soups prepared with the use of said porous granules.

11 Claims, No Drawings

METHOD FOR PREPARING POROUS SACCHARIDE GRANULES AND FOODS THEREFROM

BACKGROUND OF THE INVENTION

1. Field of the Invention

This invention relates to methods for preparing porous saccharide granules.

2. Description of the Prior Art

Methods for preparing porous granules are known which are useful for adsorbing oils therein. Japanese Kokai 75-160303 discloses a method of preparing porous granules having small bulk density by dissolving baking powder in a water solution of food stuff and spray drying the resultant mixture at a temperature higher than the decomposition temperature of baking powder and a method of preparing, oil carrying porous granules by adsorbing oils on the porous granules.

Japanese Kokai 78-23305 discloses a method of preparing dried powder by drum drying a water solution of hydrolyzate of starch having DE value of less than 18 and of preparing oil carrying powder by adsorbing oils on the resulting powder.

The porous granules or the base powder prepared by the methods of the above described Japanese Kokai, however, consists of weakly cohered particles and the oil adsorbed on the granule or the powder oozes from the granule of the powder even by a slight external pressure. These oil carrying products are easily caked during storage. These are the disadvantages of the granules or the powders prepared by the known methods.

SUMMARY OF THE INVENTION

The object of the present invention is to provide a method for preparing porous saccharide granules having strong construction, stable quality and resistance to the external pressure.

Another object of the invention is to provide a method of oil carrying porous saccharide granules which are suitable for preparing a powdered soup mix or a cake mix.

Briefly, these objects of the invention can be attained by providing a method for preparing porous saccharide granules wherein a saccharide crystallizable by heating or drying is heated at a temperature sufficient to crystallize at least a portion of the saccharide and to form conglomerated porous granules. Another object of the invention can also be attained by providing a method for preparing oil carrying porous saccharide wherein liquid oils are admixed with the porous saccharide granules. The resultant saccharide granules with adsorbed oils therein can be used for preparing a powdered soup mix or a cake mix by admixing said granules with the necessary base materials.

DESCRIPTION OF THE PREFERRED EMBODIMENT

This invention relates to methods of preparing porous saccharide granules suitable for adsorbing liquid therein which does not dissolve saccharide. The principle of the present invention is to form a firmly conglomerated porous granule consisting of several crystallized particles of saccharides cohered each other, by admixing a small amount of water with the powdered saccharide and by heating the resulting mixture at a temperature sufficient to crystallize and cohere firmly at least the wet portion of the adjacent particles of saccharide.

The granules thus formed are porous and considerably resistant to the exterior pressure. They readily adsorb liquids therein which do not dissolve saccharide, and the adsorbed liquids do not ooze from the granules even under the considerable pressure.

The saccharides to be used for the preparation of the porous granules are soluble in water and crystallizable by heating or drying. They include monosaccharides such as glucose, xylose, galactose, disaccharides such as sucrose, lactose, maltose, and polysaccharide such as raffinose, stachyose and dextrin. The saccharides are the powdered saccharides and contain usually less than 10% of moisture. These saccharides can be used solely or in the form of the mixture of more than two kinds of the saccharides. The other powdered food stuffs than the saccharides can also be admixed with saccharides.

A small amount of water is added to the saccharides to maintain a powdered mixture. The amount of water to be added to the powdered saccharides is preferably 1 to 10% and the wet saccharides, therefore, contain 1 to 20% preferably 1 to 16% of water.

If water does not disperse uniformly in the powdered mixture of saccharides, the manner and the order of admixing these components must be considered to obtain a uniformly wet powdered saccharides. Uniform dispersion of water in the powdered saccharides is one of the essential manners of the invention.

The addition of water to the powdered saccharides is to dissolve at least a portion of the surface of the saccharide particles and the amount of water to be added to the saccharides is usually enough to moisten them and to maintain their powdered form of the saccharide.

The addition of too much water makes the mixture pasty or a solution and the favorable porous granules cannot be obtained after heating. Too firmly conglomerated particles do not absorb enough oils and the solubility in water is reduced extremely. If the amount of water is small, the conglomeration of the saccharide particles after heating is not enough to obtain firmly cohered particles of saccharides.

The wet powdered saccharides are then heated under the condition sufficient to crystallize at least the wet portion of the saccharide particles, to cohere with the wet portion of the adjacent particles and to form firmly conglomerated porous granules. The heating process is carried out by the usual direct or indirect dry heating treatment using burner, oil bath or steam. The granules thus formed are porous, resistant to exterior pressure and are not caked during storage. The heating process is also the essential manner of the invention. The preferable temperature is from 100° C. to 140° C.

The favorable size of the granule is $70 \sim 1,000\mu$ and the increase of the volume per weight of the granule against that of the untreated saccharide is more than 30%.

The porous granules of the invention are suitably used as a carrier for liquids which do not dissolve saccharides, since the granules having indefinite shape and size are porous and are resistant to the external pressure. The porous granules which carry considerable amounts of liquids can be obtained only by admixing these liquids with the porous granules. These liquids are readily adsorbed in the porous granules and do not ooze from the granules even under considerable pressure.

The liquids which can be adsorbed in the granules are oils such as soybean oil, salad oil, corn oil, safflower oil, olive oil, kapok oil, sesame oil, rice oil, rape seed oil, palm oil, cotton seed oil, coconut oil, cacao butter, beef tallow, lard, butter, shortenings etc. Solid oils can be used after melting by heating.

The liquids include alcohols such as ethylalcohol, citronerol, propyleneglycol, linalol etc, esters such as sorbitan fatty acid ester, propylene-isoamylester etc, phenols such as tocopherol, isoeugenol, eugenol, ketones such as undecalactone, terpenes such as citral, coloring agent such as carotinoids, flavonoids, tars, and the above coloring agent or spices dispersed or dissolved in the above described solvents.

The preferable embodiment of the method of the invention is to use lactose and/or glucose especially glucose anhydride crystal as the saccharides and the preferable mixing ratio of lactose and glucose is from 90:10 to 70:30. The amount of water to be added to the mixture is about 1 to 10% preferably 1 to 6%.

It is preferable to admix first glucose with water and thereafter admix the mixture with lactose to obtain the uniform dispersion of water in the mixture of saccharides.

It was found effective to improve the adsorption of oils in the granules to admix at least one member selected from the group consisting of phosphoric acid salts, gums, defatted powdered milk and sodium cascinate.

Phosphoric acid salts and gums are used as the solution in water and defatted powdered milk and sodium cascinate are admixed as powders. About 20% to 60% of oil can be adsorbed in the granules.

Comparison tests were carried out to prove the favorable effect of the method of the invention.

COMPARISON TEST 1

TABLE 1

| Sample No. | glucose | water | lactose | temperature (°C.) |
|---|---|---|---|---|
| 1 | 15 | 0 | 85 | not heated |
| 2 | 15 | 4.5 | 85 | 130 |
| 3 | 15 | 4.5 | 85 | 90 |
| 4 | 15 | 4.5 | 85 | 150 |

Glucose and water were admixed and stirred, thereafter lactose was admixed with the resultant mixture according to the parts indicated in Table 1 to prepare the samples 1-4. The samples 2-4 were heated respectively up to a temperature as shown in Table 1. The structures of the granules of saccharides were observed with an electron microscope.

Samples 1-4 have clearly different structures from each other. The granules of glucose and lactose were observed as they were in sample 1. The granule of sample 3 have nearly the same structure as that of sample 1. Sample 2 shows many porous granules of various forms. Sample 4 shows porous granules. The surface of the granule illustrates the cooled and solidified state of saccharide after melting. The porous structure of the granule of sample 4 is not the same as that of sample 2. The example of the method of the present invention is merely shown in Table 1 as sample 2. All porous granules prepared according to the method of the invention have the same structures as that of sample 2.

COMPARISON TEST 2

Salad oil was added to the samples 1 to 4 of the above comparison test 1. The amount of oil adsorbed in these samples and the nature of the porous granules which carry oil therein were observed. The adsorbable limit amount of oil in the granules was determined by adding slowly the oil to the granules, mixing thoroughly the mixture, and measuring the amount of the added oil which saturates the granules. The results of the tests were shown in Table 2.

TABLE 2

| Sample | Adsorbed oil (%) | Observation of the granules |
|---|---|---|
| 1 | about 20 | |
| 2 | about 50 | Oil does not ooze from the granules even by a strong finger pressure. Readily soluble in hot water. |
| 3 | about 35 | Oil oozes from the granules under the pressure by the fingers. |
| 4 | about 35 | Oil does not ooze from the granules by a strong finger pressure. Solubility in hot water is not good. Remarkable browning is observed. |

As clearly shown in Table 2, sample 2 is superior to the other samples in the amount of adsorbed oil and the solubility in hot water.

COMPARISON TEST 3

TABLE 3

| Sample No. | glucose | water | lactose | temperature (°C.) |
|---|---|---|---|---|
| 2 | 15 | 4.5 | 85 | 130 |
| 5 | 15 | 0.5 | 85 | 130 |
| 6 | 15 | 11 | 85 | 130 |

Sample No. 2 and Samples Nos. 5 and 6 which were different from the foregoing samples in the amount of water were prepared in the same way as in the comparison test 1.

The amount of the adsorbed oil and the nature of the granules were observed in the same way as in the Comparison test 2. The results of the test were shown in Table 4.

TABLE 4

| Sample No. | Adsorbed oil (%) | Observation of the granules |
|---|---|---|
| 2 | about 50 | same as the sample No. 2 in Table 2 |
| 5 | about 30 | same as the sample No. 3 in Table 2 |
| 6 | about 30 | same as the sample No. 4 in Table 2 |

As clearly shown in Table 4, when the amount of water to be added is too much or too little, it brings about the decrease of the amount of the adsorbed oil. The preferable amount of water to be added is 1-10 parts, especially 1-6 parts by weight to 100 parts by weight of the powdered lactose and/or glucose.

COMPARISON TEST 4

Samples 7-9 were prepared by adding the various kinds of the additives as shown in Table 5.

TABLE 5

| Sample No. | glucose | water | lactose | mono sodium phosphate | defatted powdered milk | temperature (°C.) |
|---|---|---|---|---|---|---|
| 2 | 15 | 4.5 | 85 | — | — | 130 |
| 7 | 15 | 4.5 | 85 | 0.02 | — | 130 |
| 8 | 15 | 4.5 | 75 | — | 10 | 130 |
| 9 | 15 | 4.5 | 75 | 0.02 | 10 | 130 |

Mono sodium phosphate was dissolved beforehand in water and defatted powdered milk was mixed beforehand with powdered lactose. The other manners of the preparation were the same as in comparison test 1. The amount of adsorbed oil in Samples 2, 7-9 were measured in the same way as in comparison test 2. The results were shown in Table 6.

TABLE 6

| Sample No. | Adsorbed oil (%) |
| --- | --- |
| 2 | 48.9 |
| 7 | 51.8 |
| 8 | 50.1 |
| 9 | 52.5 |

As clearly shown in Table 6, the addition of mono sodium phosphate and defatted powdered milk were effective in increasing the amount of oil in the granules. The effective amount of mono sodium phosphate to be added was 0.001~0.01 parts by weight, the effective amount of defatted powdered milk was 5~50 parts by weight to 100 parts by weight of the saccharides. 0.001-0.00001 parts by weight of disodium phosphate, 0.01~0.001 parts by wt. of sodium pyrophosphate. 0.01~0.1 Parts by weight of sodium tripolyphosphate, 1~20 parts by weight of sodium cascinate, 0.002~0.2 parts by weight of gelatin and less than 5 parts by weight of sorbitol were also found effective. These effects were not limited merely in the samples illustrated in comparison test 4.

As mentioned above, the porous granules of various shapes and forms were obtained by the simple method of the present invention. The porous granules thus obtained have considerably strong structure. These porous structures are resistant to the external pressure, are not broken even under the pressure due to the accumulation during storage, and do not cause caking. The porous granules of the invention have excellent solubility in hot water and the oil adsorbed in the granules is not emulsified in hot water. Since the oil floats on the surface of hot water, they are useful for the preparation of instant soup for the noodles. The porous granules which carry oil on the granules are also useful for the preparation of a powdered soup base and a cake mix by incorporating these granules in the necessary ingredients. They impart softness, uniform dispersion of air bubbles or favorable wettability to the products.

COMPARISON TEST 5

4.5 Parts of 0.0045% di-sodium phosphate solution was added to 15 parts by weight of glucose anhydride crystal and 85 parts by weight of lactose was admixed with the resultant mixture. The mixture was heated in a metallic pan with stirring up to a temperature of 130° C. for 20 minutes. After cooling about 100 parts by weight of porous granules were obtained. The porous granules thus obtained were passed through a sieve of 16 mesh. The various kinds of liquids which did not dissolve sacharide were adsorbed in the porous granules. The result of the test was shown in Table 7.

TABLE 7

| liquid | adsorbed amount (%) |
| --- | --- |
| propylene glycol | 41.5 |
| ethyl alcohol | 41.2 |
| essential oil of ginger | 42.0 |
| onion oleoresin | 41.1 |
| extract of turmeric | 40.7 |

TABLE 7-continued

| liquid | adsorbed amount (%) |
| --- | --- |
| soybean lecithin | 43.2 |

Extract of turmeric in Table 7 consists of 13% of turmeric extract and 87% of propylene glycol. The others were liquids or viscous liquids. The amount of the adsorbed liquid in Table 7 was measured by the method described in the Comparison test 2.

As clearly shown in Table 7, the porous granules of the present invention can adsorb liquids which do not dissolve saccharide more than 40% by weight.

COMPARISON TEST 6

(This test was carried out to ascertain the effect of preventing oils from oozing from oil containing foods)

100 g of curry flake on the market added with 20 g of the porous granules obtained by the method in the comparison 5 and 100 g of the same curry flake on the market without additives were placed respectively on the separate filter paper A. The weight of the paper was measured beforehand. They were left in the thermostat keeping at a temperature of 45° C. for a day. The weight of the filter paper B which adsorbed the exuded oil was measured. The amount of the exuded oil was determined by reducing the weight of the filter paper A from the weight of the filter paper B. The result of the test was shown in Table 8.

TABLE 8

| Sample | rate of exuded oil (%) |
| --- | --- |
| curry flake with the porous granules | 0.2 |
| curry flake without adding porous granules | 3.2 |

As clearly shown in table 2 the amount of the oil transuded from the curry flake added with porous granules is far smaller than that of the oil transuded from the curry flake alone.

Therefore the porous granules of the present invention enable various kinds of liquids which do not dissolve saccharide to transform into powder. Consequently the granules have the advantage of the physical property as powder which is readily measured and is uniformly mixed with the other powdered materials. As the porous granules of the present invention is mainly composed of saccharide, they can easily disperse the liquids in an aqueous solution.

The porous saccharide granules which adsorb oils therein are used for preparing a cake mix by admixing said granules with wheat flour, baking powder and, if required, further with sugar, emulsifier, powdered milk and powdered egg white. The cake mix thus prepared is conveniently used for cooking cakes by the housewives.

The conventional cake mix in the market is usually prepared using oil carrying materials which are made by admixing oils with starch, emulsifier, gelatin, casein and water, emulsifying and spray drying the mixture. The cake prepared with the cake mix has not uniform texture, has crack on the surface and has not softness.

The cake mix of the invention can be prepared by admixing the ingredients other than that of the above described materials such as corn starch, defatted powdered milk, powdered cocoa, spices (cinnamon, clove, ginger, caldamon), salts, coconut, almond and coloring agents. It is preferable to use 5 to 25% by weight of oil against the weight of cake mix.

The cake prepared from the cake mix of the invention is superior to the conventional one in its texture, palatability and appearance.

The porous granules which carry oils therein are used also for preparing a powdered soup mix by admixing these granules with a powdered soup base.

The powdered soup mix of the invention is conveniently used for the soup with instant noodles. Oils are floating usually on the soup with noodles. Therefore, powdered soup and oils are packed usually in the separate packages. Small drops oil remain in the package and the oil will spoil the fingers when the packages are opened. The powdered soup mix can avoid the disadvantage of the conventional packages of the additives, since the soup mix of the invention can carry the considerable amount of oil in the porous granules and maintain a powder form with the other powdered soup base.

The powdered soup mix is useful as the soup for Chinese noodles, soup of Chinese style, and for Japanese chowder.

The powdered soup base to be incorporated with the porous granules which carry oils include powdered meat extract such as beef, chicken and pork, powdered vegetable extract (onion, carrot, Chinese cabbage and mushroom), spices such as pepper, garlic and ginger, powdered meat or vegetables, powdered soy sauce, powdered soy paste, salts, sugar, organic acid such as citric acid and succinic acid, amino acids such as sodium glutamate and glycine, nucleic acids such as sodium guanylate and sodium inosinate.

EXAMPLE 1

10 Parts by weight of water was sprayed over 100 parts by weight of lactose and mixed by stirring.

The resultant mixture was heated in a heat-resistant metalic pan with stirring up to a temperature of 140° C. to prepare about 100 parts by weight of porous granules having considerably strong construction.

EXAMPLE 2

1 Part by weight of water was admixed with 100 parts by weight of glucose. The resultant mixture was heated in a heat resistant metalic pan with stirring up to a temperature of 110° C. to prepare about 100 parts by weight of porous granules having considerably strong construction.

EXAMPLE 3

10 Parts by weight of glucose was added with 2 parts by weight of water and 90 parts by weight of lactose was added to the resultant mixture. Then 8 parts by weight of water was added and mixed thereafter. 110 Parts by weight of the resultant powdery mixture was heated and stirred up to a temperature of 120° C. in a heat-resistant metalic pan to prepare about 100 parts by weight of porous granules of various forms having considerably strong construction. Then 110 parts by weight of soybean oil was added to about 100 parts by weight of the porous granules. The resultant mixture was added and stirred to prepare the porous granules of various forms containing about 54% by weight of the oil.

EXAMPLE 4

4.5 Parts by weight of water in which 0.002 parts by weight of disodium phosphate was dissolved was admixed with 15 parts by weight of glucose. Thereafter 75 parts by weight of lactose and 10 parts by weight of sodium cascinate were admixed with the resultant mixture. 104.5 Parts by weight of the resultant powdery mixture was heated and stirred up to a temperature of 130° C. in a heat-resistant metalic pan to prepare about 100 parts by weight of porous granules of various forms having considerably strong construction. Then 150 parts by weight of salad oil was added to 100 parts by weight of the porous granules. The resultant mixture was mixed and stirred to prepare porous granules containing about 60% by weight of the oil.

EXAMPLE 5

6 Parts by weight of water was added and mixed with 10 parts by weight of glucose and then 90 parts by weight of lactose was added and mixed thereafter. 106 Parts by weight of the resultant powdery mixture was heated in a heat-resistant metalic pan with stirring up to a temperature of 130° C. to prepare 100 parts by weight of porous granules having considerably strong construction.

EXAMPLE 6

6 Parts by weight of water was sprayed over the mixture of 100 parts by weight of lactose and 15 parts by weight of sodium cascinate and mixed. The resultant mixture was heated in a heat resistant metalic pan with stirring up to a temperature of 140° C. to prepare about 100 parts by weight of porous granules of various forms having considerably strong construction.

EXAMPLE 7

20 g of brandy was adsorbed in 80 g of the porous granules obtained in example 1 to obtain 100 g of powdery alcohol.

20 g of brandy was adsorbed to 80 g of the porous granules of various forms obtained in example 7 to prepare powdery alcohol. 30 g of said powdery alcohol was mixed with 50 g of wheat flour, 40 g of conventional powdery oils obtained in the market, 30 g of sugar, 2 g of baking powder, 5 g of defatted powdered milk and 0.5 g of flavor. 50 cc of water and 50 g of whole egg were mixed with the resultant mixture and the mixture was baked in an oven at a temperature to obtain sponge cake having flavour of brandy.

EXAMPLE 8

40 g of paprika, water soluble liquid coloring agent was added with stirring to 60 g of the porous granules of various forms obtained in example 6 to prepare 100 g of powdery coloring agent of paprika.

40 g of paprika was added with stirring to 60 g of porous granules obtained in example 8 to prepare powdery coloring agent of paprika, 0.1 g of powdery paprika was mixed with 60 g of granulated sugar, 1.9 g powdery orange flavor and 38 g of powdered milk. The mixture was added to 300 cc of water mixed and cooled to obtain orange sherbet.

EXAMPLE 9

9 Parts by weight (hereinafter the part is indicated by weight) of water in which 0.004 parts of disodium phosphate was dissolved beforehand was admixed with 30 parts of glucose. Thereafter 150 parts of lactose and 20 parts of sodium cascinate were admixed with the resultant mixture. 209 parts of the resultant powdery mixture was heated with stirring up to a temperature of 130° C. in a heat-resistant metalic pan to prepare about 200 parts of porous granules of various forms having considerably strong structure. 200 Parts of shortening with which 4 parts of glycorol fatty acid ester was admixed beforehand was added to 200 parts of said porous granules and mixed with stirring to obtain powder containing 50% of oil.

100 Parts of granules containing oil, 100 parts of wheat flour, 60 parts of sugar, 4 parts of baking powder, 1.6 parts of table salt and 2 parts of sucrose fatty acid ester were admixed to prepare about 267 parts of cake-mix. 50 Parts of egg and 30 parts of water were mixed thoroughly with 170 parts of cake-mix thus obtained and the mixture was baked in an oven at 180° C. for 20 minutes to prepare cake having spongy texture, excellent palatabioity and appearance.

EXAMPLE 10

60 Parts of granules containing oil prepared by the method of example 9, 70 parts of wheat flour, 20 parts of conventional powdered oil obtained in the market (containing 70% of oil), 20 parts of sugar, 0.2 parts of baked salt, 10 parts of defatted powdered milk, 0.2 parts of baking powder and 0.1 parts of flavor were admixed to obtain about 180 parts of cake-mix.

40 Parts of egg admixed thoroughly with 176 parts of cake-mix thus obtained. The resultant mixture was pressed out from the bag on a baking board and baked in an oven at 160° C. for 20 minutes to prepare cookie having excellent texture, palatability and appearance.

EXAMPLE 11

4.5 Parts of water was admixed with 15 parts of glucose, and 85 parts of lactose was admixed with the resultant mixture. 104.5 Parts of the resultant powdered mixture was heated with stirring up to a temperature of 130° C. in a heat-resistant metalic pan to prepare 100 parts of porous granules of various forms having considerably strong structure. Then 40 parts of edible vegetable oil having the flavor of sesame oil was added with stirring to the porous granules to prepare about 140 parts of granules containing oil. 35 Parts of said granules containing oil, 7 parts of powdered chiken extracts, 5 parts of meat extracts, 35 parts of table salt, 8 parts of glucose, 5 parts of amino acid powder, 0.7 parts of mixed spices and 5 parts of sodium glutamate were admixed to obtain powdered soup mix for Chinese noodles.

What is claimed is:

1. A method for preparing porous saccharide granules, comprising:
    (a) moistening saccharide granules to a moisture content of 1 to 20 wt. % water thereby forming moistened saccharide granules which maintain the form of granules; and
    (b) heating said moistened saccharide granules to a temperature between 100° C. and 140° C. sufficient to crystallize said granules.

2. The method of claim 1, which further comprises, at prior to heating said moistened saccharide granules, said moistened saccharide granules are admixed with at least one substance selected from the group consisting of phosphoric acid salts, gums, defatted powdered milk and sodium caseinate.

3. The method of claim 1, wherein said moistened saccharide granules are prepared by admixing a sufficient amount of water with the granules to attain a moisture content of 1–20 wt. %.

4. The method of claim 1, wherein said moistened saccharide granules are prepared by admixing from 1–10 wt. % water with unmoistened saccharide granules.

5. The method of claim 4, wherein the amount of water added to said unmoistened saccharide granules ranges from 1–6 wt. %.

6. A liquid containing porous saccharide granule product comprising: the porous saccharide granule product obtained from the process of claim 1 or 2 having a liquid absorbed thereon selected from the group consisting of soybean oil, salad oil, corn oil, safflower oil, olive oil, kapok oil, sesame oil, rice oil, rape seed oil, palm oil, cotton seed oil, coconut oil, cacao butter, beef tallow, lard, butter shortenings, ethylalcohol, citronerol, propyleneglycol, linalol, esters, phenols, ketones, terpenes and coloring agents.

7. A method for preparing a powdered soup mix, which comprises: admixing the liquid containing porous saccharide granule product of claim 6 with a powdered soup base prepared by admixing a meat extract, a powdered vegetable extract, spices, powdered meat or vegetables, powdered soy sauce, powdered soy paste, salts, sugar, and organic acid, amino acid or nucleic acid in some combination depending upon the type of soup desired.

8. The powdered soup mix prepared by the process of claim 7.

9. A method of preparing a cake mix, which comprises: admixing the liquid containing porous saccharide granule product of claim 6 with wheat flour and baking powder.

10. The method of claim 9, wherein sugar and emulsifier, powdered milk and powdered egg white is further added to said mixture.

11. The mixture prepared by the process of claim 9.

* * * * *

UNITED STATES PATENT AND TRADEMARK OFFICE
CERTIFICATE OF CORRECTION

PATENT NO. : 4,382,967

DATED : May 10, 1983

INVENTOR(S) : Daikichi Koshida et al

It is certified that error appears in the above-identified patent and that said Letters Patent is hereby corrected as shown below:

On the title page, Item (22) should read

--(22) January 27, 1981 --

Signed and Sealed this

Thirteenth Day of September 1983

[SEAL]

Attest:

GERALD J. MOSSINGHOFF

Attesting Officer

Commissioner of Patents and Trademarks